United States Patent
Boyd et al.

(10) Patent No.: US 9,598,438 B2
(45) Date of Patent: Mar. 21, 2017

(54) SUGAR DERIVATIVES COMPRISING SULFUR-CONTAINING MOIETIES AND METHODS OF MAKING SAME AND METHODS OF USING THE SAME FOR THE TREATMENT OF MPS IIIC

(71) Applicant: Amicus Therapeutics, Inc., Cranbury, NJ (US)

(72) Inventors: Robert Boyd, Horsham, PA (US); Gary Lee, West Windsor, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 14/620,283

(22) Filed: Feb. 12, 2015

(65) Prior Publication Data

US 2015/0225420 A1 Aug. 13, 2015

Related U.S. Application Data

(60) Provisional application No. 61/938,924, filed on Feb. 12, 2014.

(51) Int. Cl.

| | |
|---|---|
| *C07D 498/14* | (2006.01) |
| *C07D 497/04* | (2006.01) |
| *A61K 31/4365* | (2006.01) |
| *C07D 211/56* | (2006.01) |
| *A61K 31/45* | (2006.01) |
| *A61K 45/06* | (2006.01) |
| *A61K 31/437* | (2006.01) |
| *C07D 498/04* | (2006.01) |
| *C07D 513/04* | (2006.01) |
| *C07D 211/46* | (2006.01) |

(52) U.S. Cl.
CPC .......... *C07D 498/14* (2013.01); *A61K 31/437* (2013.01); *A61K 31/4365* (2013.01); *A61K 31/45* (2013.01); *A61K 45/06* (2013.01); *C07D 211/46* (2013.01); *C07D 211/56* (2013.01); *C07D 497/04* (2013.01); *C07D 498/04* (2013.01); *C07D 513/04* (2013.01)

(58) Field of Classification Search
None
See application file for complete search history.

(56) References Cited

U.S. PATENT DOCUMENTS

| 6,774,140 B1 | 8/2004 | Wong et al. |
| 2011/0091442 A1 | 4/2011 | Boyd et al. |

FOREIGN PATENT DOCUMENTS

| WO | WO-2008/025170 | 3/2008 |
| WO | WO-2013/011098 | 1/2013 |
| WO | WO-2013/148103 | 10/2013 |

OTHER PUBLICATIONS

Furneaux, Richard H. "2-Acetamido-1,2-dideoxynojirimycin: an improved synthesis." Tetrahedron, 49(42), 9605-12 1993.*
Abdallah "Synthesis of a Carbon-Linked Mimic of the Disaccharide Component of the Tumor-Related SialylTn Antigen" Angew. Chem. Int. Ed. 2003, 42, 5209-5212.*
Dorwald F. A. Side Reactions in Organic Synthesis, 2005, Wiley: VCH, Weinheim p. IX of Preface p. 1-15, 41.*
Feldhammer "Sanfilippo Syndrome Type C: Mutation Spectrum in the Heparan Sulfate Acetyl-CoA: a-Glucosaminide N-Acetyltransferase (HGSNAT) Gene" Human Mutation vol. 30, Issue 6, 2009, 918-925.*
Ficko-Blean "The Structural and mechanistic insight into the basis of mucopolysaccharidosis IIIB" PNAS May 6, 2008 vol. 105 No. 18 6560-6565.*
Wolff (Medicinal Chemistry) summarizes the state of the prodrug art. Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Rautio et. al. "Prodrugs: design and clinical Applications" Nature Reviews Drug Discovery 2008, 7, 255-270.*
Beaumont "Design of Ester Prodrugs to Enhance Oral Absorption of Poorly Permeable Compounds: Challenges to the Discovery Scientist" Current Drug Metabolism, 2003, 4, 461-485.*
Baell "New Substructure Filters for Removal of Pan Assay Interference Compounds (PAINS) from Screening Libraries and for Their Exclusion in Bioassays" J. Med. Chem. 2010, 53, 2719-2740 2719.*
Jensen "Synthesis and investigation of L-fuco- and D-glucurono-azafagomine" J. Chem. Soc., Perkin Trans. 1, 2002, 1190-1198.*
Bentley "Solvolyses of Secondary Sulfonates in Aqueous Ethanol and Acetone. Nonlinear mY Relationships due to Leaving Group and Medium Effects" Journal of Organic Chemistry 1981, 46, 38-42.*
Shriver "Heparin and Heparan Sulfate: Analyzing Structure and Microheterogeneity" Handb Exp Pharmacol. 2012 ; (207): 159-176.*
Partial International Search Report in PCT/US2015/015557, dated Mar. 31, 2015, 6 pgs.
PCT International Search Report and Written Opinion in PCT/US2015/015557, mailed Jul. 29, 2015, 17 pages.
PCT Preliminary Report on Patentability in PCT/US2015/015557 dated Aug. 25, 2016, 11 pages.

\* cited by examiner

*Primary Examiner* — David K O'Dell
(74) *Attorney, Agent, or Firm* — Servilla Whitney LLC

(57) ABSTRACT

Described herein are modified sugar, iminosugar and aza-sugar compounds and methods of making same. One or more of these modified compounds contain sulfates, sulfites, sulfamates and/or sulfonamides. Also described are pharmaceutical compositions/formulations comprising these compounds, as well as methods using these modified sugar compounds for the treatment of MPS IIIC (also known as Sanfilippo Type C).

4 Claims, No Drawings

SUGAR DERIVATIVES COMPRISING SULFUR-CONTAINING MOIETIES AND METHODS OF MAKING SAME AND METHODS OF USING THE SAME FOR THE TREATMENT OF MPS IIIC

CROSS-REFERENCE TO RELATED APPLICATIONS

This application claims the benefit under 35 U.S.C. §119 (e) to U.S. Provisional Application No. 61/938,924, filed Feb. 12, 2014, the entire contents of which are incorporated herein by reference in their entirety.

TECHNICAL FIELD

This invention generally pertains to novel modified sugar compounds, and more particularly to sugars, iminosugars and azasugars containing sulfates, sulfites, sulfamates, and sulfonamides.

BACKGROUND

Lysosomal storage diseases/disorders describe several dozen rare genetic metabolic disorders. Lysosomal storage disorders are caused by lysosomal dysfunction usually as a consequence of deficiency of an enzyme used in the metabolism of lipids, glycoproteins or glycosaminoglycans (formerly known as mucopolysaccharides). Lysosomes break down unwanted matter via enzymes. Lysosomal disorders occur when a particular enzyme is compromised or missing. As a result, the undesired substances accumulate in the cell.

Lysosomal storage diseases can cause severe symptoms and/or can severely shorten a patient's lifespan. There are no cures for lysosomal storage diseases and treatment is mostly symptomatic, although enzyme replacement therapy (ERT) have been tried with some success. However, at least some enzymes utilized for ERT cannot pass the blood-brain barrier, thereby limiting their effect on neurological symptoms, which can be quite severe in some lysosomal storage diseases.

For example, mucopolysaccharidoses (MPS) are diseases in which one or more steps in the metabolic pathway for the degradation of glycosaminoglycans (GAGS) are compromised, and the body is unable to properly break down the glycosaminoglycans. The compromised ability of the body to produce α-Glucosamide N-acetyltransferase results in MPS IIIC, also known as Sanfilippo syndrome type C. The clinical symptoms of Sanfilippo syndrome include behavioral problems, intellectual disability, coarse facial features and walking difficulties, and generally, people afflicted with the syndrome have lifespans extending only into their teenage years. Currently, there is no known treatment that satisfactorily addresses the above symptoms, particular the neurological ones. Although the affected enzyme may be produced and given to the patient as ERT, the ERT enzyme does not cross the blood-brain barrier, and therefore cannot reach the brain to treat the cause of the neurological symptoms.

Pharmacological chaperones can help to stabilize the defective enzymes produced by patients that have lysosomal storage disorders. However, chaperones are often specific to certain lysosomal storage disorders, and many diseases still have no known medicines. There is thus a need for new therapeutic compounds that can be used to prevent and/or treat various lysosomal storage disorders such as MPSIIIC that provide patients with a higher quality of life and achieve a better clinical outcome.

SUMMARY

One aspect of the invention pertains to a compound having a structure represented by formula I or II:

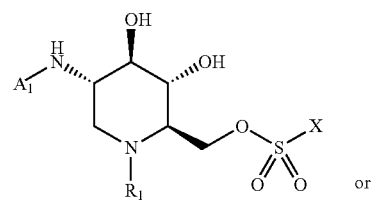

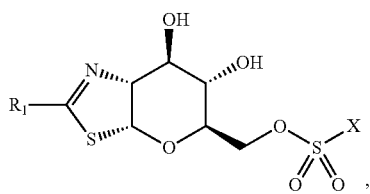

wherein:

$A_1$ is —$COR_2$, —$SO_2R_2$, —$CONR_2R_3$, —$SO_2NR_2R_3$;

$R_1$, $R_2$, $R_3$ are each independently H, arylalkyl, aryl, or $C_{1-4}$ alkyl; and X is —OH or —$NR_1R_2$; or a pharmaceutically acceptable salt, solvate, or prodrug thereof. In one or more embodiments, the compound has a structure represented by formula Ia:

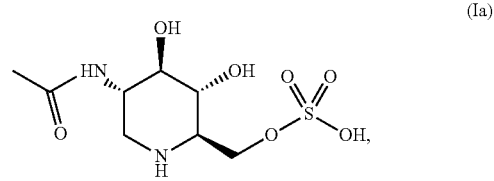 [SMILES: CC(=O)N[C@H]1CN[C@H](COS(=O)(=O)O)[C@@H](O)[C@@H]1O]

or a pharmaceutically acceptable salt, solvate, or prodrug thereof.

Another aspect of the invention pertains to a compound having a structure represented by formula III or IV:

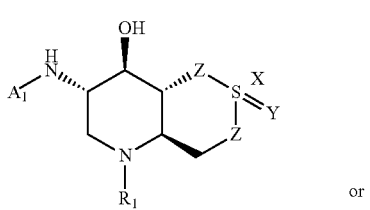

or

-continued

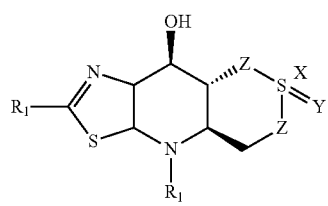
(IV)

wherein:

$A_1$ is —$COR_2$, —$SO_2R_2$, —$CONR_2R_3$, —$SO_2NR_2R_3$;

$R_1$, $R_2$ and $R_3$ are each independently H, arylalkyl, aryl, or $C_{1-4}$ alkyl;

X and Y are each independently O or a lone pair of electrons; and each Z is independently O or NH; or a pharmaceutically acceptable salt, solvate, or prodrug thereof. In one or more embodiments, the compound has a structure represented by formula IIIa:

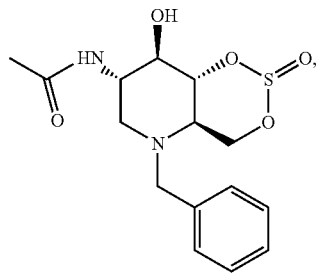
(IIIa)

or or a pharmaceutically acceptable salt, solvate, or prodrug thereof. In some embodiments, the compound has a structure represented by formula IIIb:

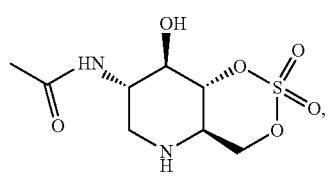
(IIIb)

or a pharmaceutically acceptable salt, solvate, or prodrug thereof.

A third aspect of the invention pertains to a compound having a structure represented by any of formulae (V)-(XI):

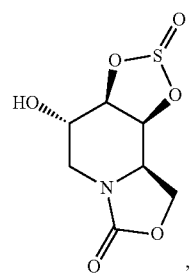
(V)

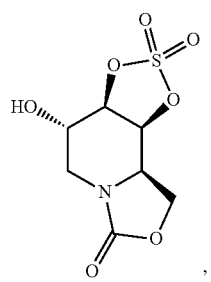
(VI)

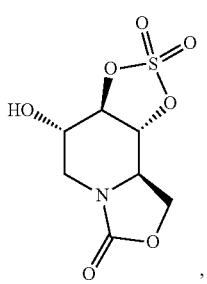
(VII)

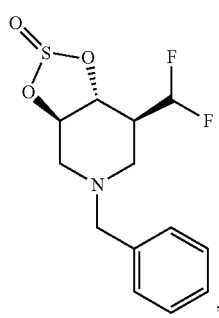
(VIII)

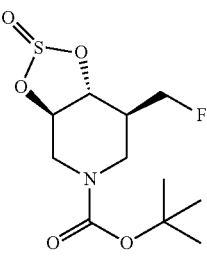
(IX)

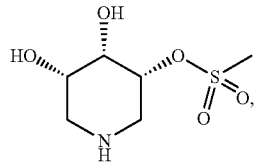
(X)

-continued

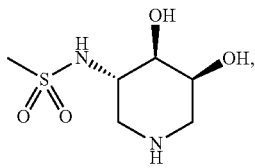

(XI)

or or a pharmaceutically acceptable salt, solvate, or prodrug thereof.

Other aspects of the invention relate to methods of making compounds having a structure represented by any of formulae (V)-(XI). In one or more embodiments, the invention pertains to a method of making the compound having a structure represented by formula (V), the method comprising reacting 1-deoxygalactonojirimycin with EtOCOCl to produce an intermediate; and reacting the intermediate with $SO_2Cl$ and pyridine.

In some embodiments, the invention pertains to a method of making the compound having a structure represented by formula (VI), the method comprising reacting 1-deoxygalactonojirimycin with EtOCOCl to produce an intermediate; and reacting the intermediate with $SO_2Cl_2$ and pyridine.

In one or more embodiments, the invention pertains to a method of making the compound having a structure represented by formula (VII), the method comprising reacting 1-deoxynojirimycin with EtOCOCl to produce an intermediate; and reacting the intermediate with $SO_2Cl_2$ and pyridine.

In some embodiments, the invention pertains to a method of making the compound having a structure represented by formula (X), the method comprising reacting a compound having a structure represented by:

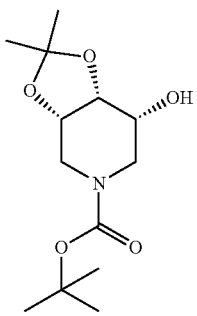 [SMILES: CC(C)(C)OC(=O)N1C[C@@H](O)[C@H]2OC(C)(C)O[C@H]2C1]

with methanesulfonyl chloride (MsCl) and $NET_3$ to produce an intermediate; and reacting the intermediate with HCl.

In some embodiments, the invention pertains to a method of making the compound having a structure represented by formula (XI), the method comprising reacting a compound having a structure represented by:

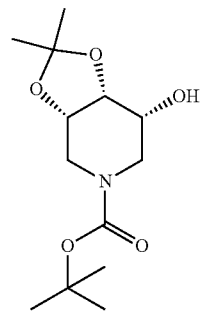 [SMILES: CC(C)(C)OC(=O)N1C[C@@H](O)[C@H]2OC(C)(C)O[C@H]2C1]

with $LiN_3$ to produce an intermediate; and reacting the intermediate with Pd/C and $H_2$, $MeSO_2Cl$ and $NEt_3$, and HCl.

In one or more embodiments, the invention pertains to a method of making the compound having a structure represented by formula (IX), the method comprising reacting a compound having a structure represented by:

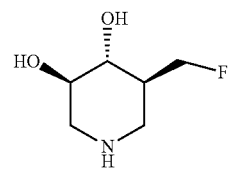

with $SO_2Cl$ and pyridine.

In some embodiments, the invention pertains to a method of making the compound having a structure represented by formula (VIII), the method comprising reacting a compound having a structure represented by:

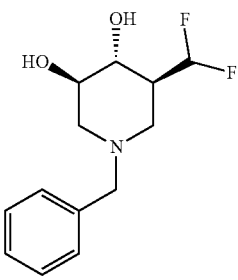 [SMILES: O[C@H]1[C@H](O)CN(Cc2ccccc2)C[C@@H]1C(F)F]

with $SO_2Cl$ and pyridine.

Another aspect of the invention pertains to a pharmaceutical composition comprising a compound according to any of the above compounds; and at least one pharmaceutically acceptable carrier. In yet another aspect, the invention relates to a method of making the pharmaceutical composition. In one or more embodiments, the method comprises adding to at least one pharmaceutically acceptable carrier a compound having a structure represented by any of formulae I-XI.

Yet another aspect of the invention pertains to a method of preventing and/or treating MPS IIIC. In one or more embodiments, the method comprises administering to a patient in need thereof a therapeutically effective amount of a compound having a structure represented by formula I or II:

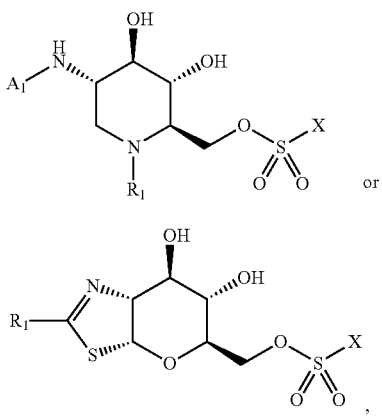

(I)

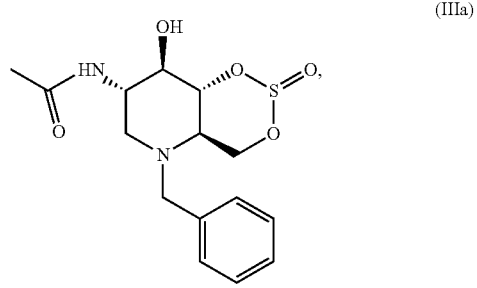

(II)

wherein:
A$_1$ is —COR$_2$, —SO$_2$R$_2$, —CONR$_2$R$_3$, —SO$_2$NR$_2$R$_3$;
R$_1$, R$_2$, R$_3$ are each independently H, arylalkyl, aryl, or C$_{1-4}$ alkyl; and
X is —OH or —NR$_1$R$_2$; or
a pharmaceutically acceptable salt, solvate, or prodrug thereof. In some embodiments, the compound has a structure represented by formula Ia:

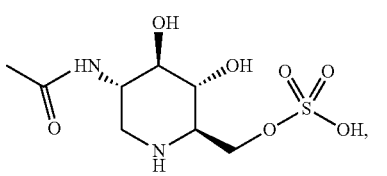

(Ia)

or
a pharmaceutically acceptable salt, solvate, or prodrug thereof.

In one or more embodiments of the invention, the method comprises administering to a patient in need thereof a therapeutically effective amount of a compound having a structure represented by: formula III or IV:

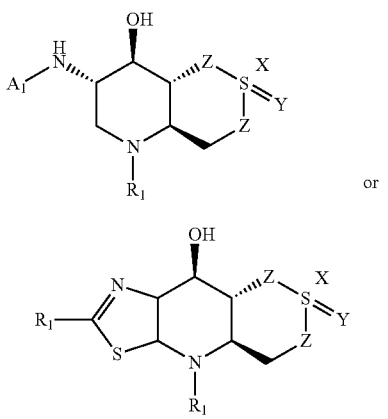

(III)

(IV)

wherein:
A$_1$ is —COR$_2$, —SO$_2$R$_2$, —CONR$_2$R$_3$, —SO$_2$NR$_2$R$_3$;
R$_1$, R$_2$ and R$_3$ are each independently H, arylalkyl, aryl, or C$_{1-4}$ alkyl;

X and Y are each independently O or a lone pair of electrons; and
each Z is independently O or NH; or
a pharmaceutically acceptable salt, solvate, or prodrug thereof. In further embodiments, the compound has a structure represented by formula IIIa:

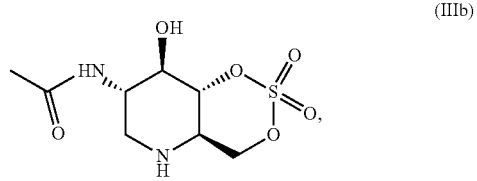 [SMILES: CC(=O)N[C@H]1CN[C@@H]2COS(=O)(=O)O[C@H]2[C@@H]1O]

(IIIa)

or
or a pharmaceutically acceptable salt, solvate, or prodrug thereof. In some embodiments, the compound has a structure represented by formula IIIb:

(IIIb)

or
or a pharmaceutically acceptable salt, solvate, or prodrug thereof.

Another aspect of the invention pertains to a kit comprising:
a. a container having an effective amount of a compound having a structure represented by: formula I or II:

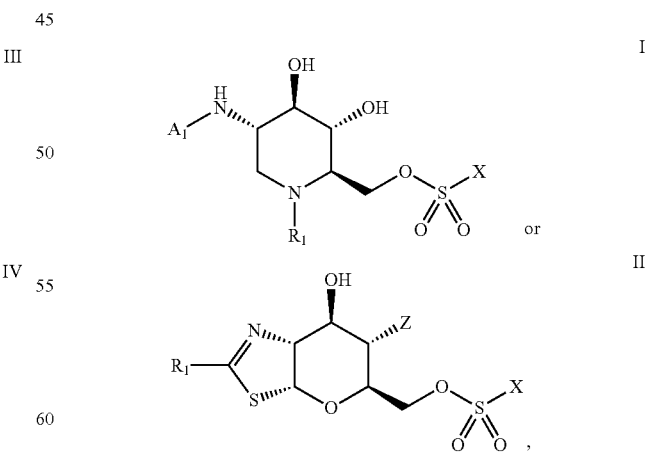

(I)

(II)

wherein:
A$_1$ is —COR$_2$, —SO$_2$R$_2$, —CONR$_2$R$_3$, —SO$_2$NR$_2$R$_3$;
R$_1$, R$_2$, R$_3$ are each independently H, arylalkyl, aryl, or C$_{1-4}$ alkyl; and X is —OH or —NR$_1$R$_2$; or a pharmaceutically acceptable salt, solvate, or prodrug thereof, or any combination of two or more thereof; and b. instructions for using the same to prevent and/or treat MPS IIIC.

In one or more embodiments, the compound has a structure represented by formula Ia:

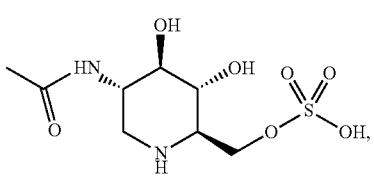

(Ia)

or a pharmaceutically acceptable salt, solvate, or prodrug thereof.

Yet another aspect of the invention pertains to a kit comprising:

a. a container having an effective amount of a compound having a structure represented by: formula III or IV:

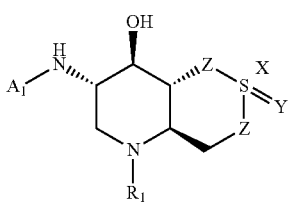

III or

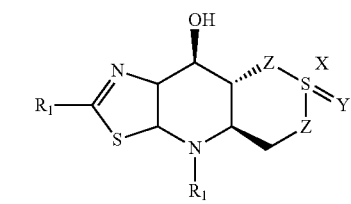

IV wherein:

A$_1$ is —COR$_2$, —SO$_2$R$_2$, —CONR$_2$R$_3$, —SO$_2$NR$_2$R$_3$;

R$_1$, R$_2$ and R$_3$ are each independently H, arylalkyl, aryl, or C$_{1-4}$ alkyl;

X and Y are each independently O or a lone pair of electrons; and each Z is independently O or NH;

or a pharmaceutically acceptable salt, solvate, or prodrug thereof, or any combination of two or more thereof; and b. instructions for using the same to prevent and/or treat MPS IIIC.

In some embodiments of this aspect, the compound has a structure represented by formula IIIa:

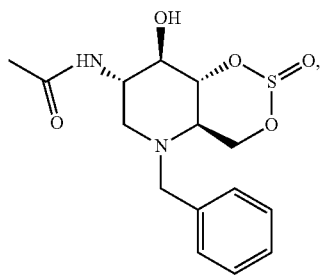

(IIIa)

or or a pharmaceutically acceptable salt, solvate, or prodrug thereof. In one or more embodiments, the compound has a structure represented by formula IIIb:

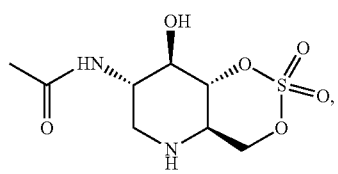

(IIIb)

or or a pharmaceutically acceptable salt, solvate, or prodrug thereof.

In one or more embodiments, the method of preventing and/or treating MPS IIIC further comprises administering to the patient a second therapeutic agent comprising a recombinant MPS IIIC enzyme. Similarly, in some embodiments, the kit further comprises a second therapeutic agent comprising a recombinant MPS IIIC enzyme.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Described herein are modified sugar, iminosugar and azasugar compounds. These modified compounds may contain sulfates, sulfites, sulfamates and/or sulfonamides. Also described are pharmaceutical compositions/formulations comprising these compounds. It is thought that these compounds may have utility as potential pharmacological chaperones and/or inhibitors of one or more enzymes that are defective in lysosomal storage disorders. While not wishing to be bound to any particular theory, it is thought that one or more of these compounds are suitable as pharmacological chaperones because they may resemble one or more target substrates of one or more enzymes.

For example, certain of these modified sugar compounds containing sulfates, sulfites, sulfamates and/or sulfonamides may be suitable for use as pharmacological chaperones and/or inhibitors of α-Glucosamide N-acetyltransferase. This enzyme is involved in the metabolic pathway for the degradation of heparan sulfate as shown in Scheme 1 below:

Scheme 1:
Degradation of Heparan Sulfate by α-Glucosamide N-acetyltransferase

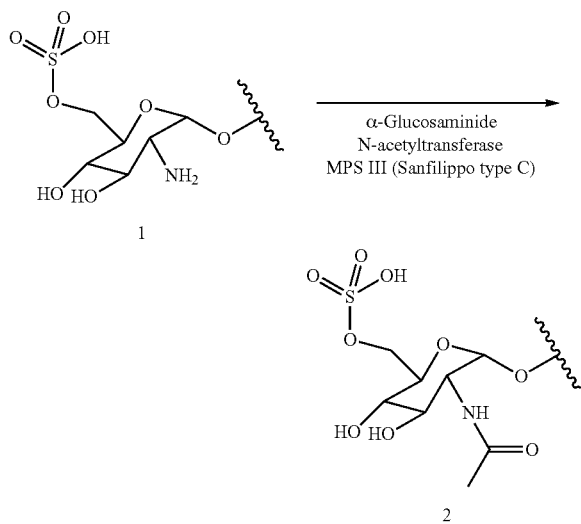

As shown in the scheme above, heparan sulfate acetyl-coA: α-Glucosamide N-acetyltransferase (HGSNAT) catalyzes the aceylation of intermediate 1. As dysfunction in this enzyme is associated with MPS IIIC, these sugar compounds are suitable for use in the treatment of MPS IIIC because they resemble the target substrate shown in Scheme 1 above. Also described are kits comprising these compounds and instructions for the treatment of MPS IIIC.

As used herein, the term "pharmacological chaperone," or sometimes "specific pharmacological chaperone" ("SPC"), refers to a molecule that specifically binds to a protein, particularly an enzyme, and has one or more of the following effects: (i) enhancing the formation of a stable molecular conformation of the protein (both wild-type and mutant proteins); (ii) enhances proper trafficking of the protein from the endoplasmic reticulum (ER) to another cellular location, preferably a native cellular location, i.e., preventing ER-associated degradation of the protein; (iii) preventing aggregation of conformationally unstable, i.e., misfolded proteins; (iv) restoring or enhancing at least partial wild-type function, stability, and/or activity of the protein; and/or (v) improving the phenotype or function of the cell harboring a mutant protein. Thus, a pharmacological chaperone is a molecule that specifically binds to a protein, resulting in proper folding, trafficking, non-aggregation, and/or activity of that protein. In the context of the present invention, the specific pharmacological chaperones are substrates, or substrate analogs or derivatives, of the enzymes.

The wild-type activity/amount can be increased in vivo and/or for co-formulation for ERT. The mutant can be stabilized/enhanced in vivo through the endoplasmic reticulum, etc. Both mutant and wild type proteins in the same patient can be stabilized if both are present (such as the case with X-linked diseases). Thus, one or more embodiments of the invention pertain to enhancement of the enzyme (recombinant or native/mutant) and different types of administration (co-formulation with recombinant, co-administration with recombinant, monotherapy for the mutant enzyme that is endogenously produced, and any combination of the above.)

As used herein, the term "substrate" refers to a molecule that is acted upon (i.e., modified) by an enzyme. According to the present invention, this term refers to an enzyme's natural or physiological substrate that is unmodified by human intervention.

The terms "therapeutically effective dose" and "effective amount" refer to the amount of the specific pharmacological chaperone that is sufficient to result in a therapeutic response. A therapeutic response may be any response that a user (e.g., a clinician) will recognize as an effective response to the therapy, including the foregoing symptoms and surrogate clinical markers. Thus, a therapeutic response will generally be an amelioration of one or more symptoms of a disease or disorder, e.g., a lysosomal storage disease, such as those known in the art for the disease or disorder, e.g., neurological symptoms.

As used herein the term "patient" means a mammal (e.g., a human).

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

As used herein, "aryl" refers to aromatic radicals having in the range of about 6 to about 14 carbon atoms such as phenyl, naphthyl, tetrahydronapthyl, indanyl, biphenyl. The term "arylalkyl" refers to an aryl group as defined above directly bonded to an alkyl group, e.g., —$CH_2C_6H_5$, and —$C_2H_4C_6H_5$.

Compounds

One aspect of the invention pertains to a compound having a structure represented by formula I or II:

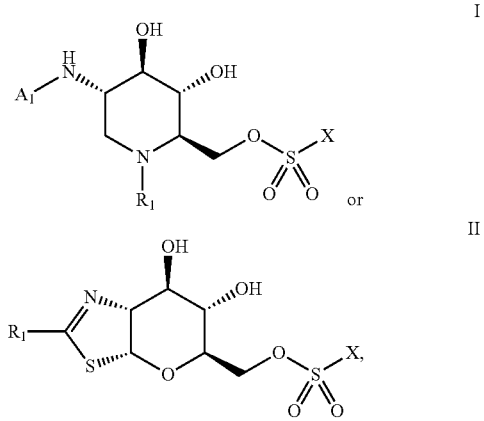

wherein:
$A_1$ is —$COR_2$, —$SO_2R_2$, —$CONR_2R_3$, —$SO_2NR_2R_3$;
$R_1$, $R_2$, $R_3$ are each independently H, arylalkyl, aryl, or $C_{1-4}$ alkyl; and X is —OH or —NR$_1$R$_2$; or a pharmaceutically acceptable salt, solvate, or prodrug thereof. In some embodiments, the compound has a structure represented by formula Ia:

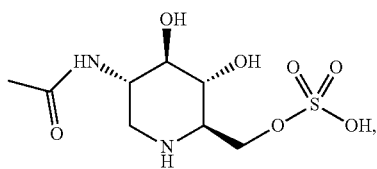
(Ia)

or a pharmaceutically acceptable salt, solvate, or prodrug thereof.

Another aspect of the invention pertains to a compound having a structure represented by formula III or IV:

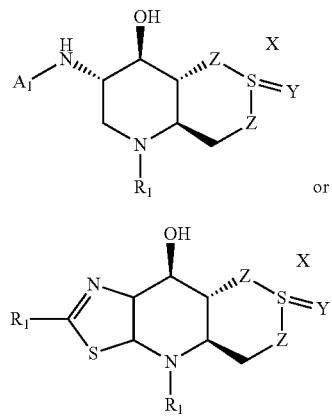

wherein:

A$_1$ is —COR$_2$, —SO$_2$R$_2$, —CONR$_2$R$_3$, —SO$_2$NR$_2$R$_3$;

R$_1$, R$_2$ and R$_3$ are each independently H, arylalkyl, aryl, or C$_{1-4}$ alkyl;

X and Y are each independently O or a lone pair of electrons; and each Z is independently O or NH; or a pharmaceutically acceptable salt, solvate, or prodrug thereof.

In one or more embodiments, the compound has a structure represented by formula IIIa:

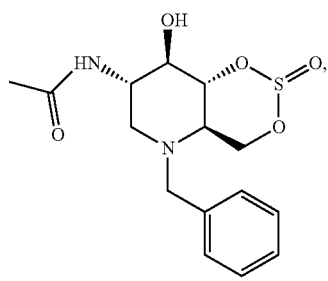
(IIIa)

or a pharmaceutically acceptable salt, solvate, or prodrug thereof. The compound of formula IIIa may be referred to as N-((4aR,7S,8R,8aR)-5-benzyl-8-hydroxy-2-oxidohexahydro-4H-[1,3,2]dioxathiino[5,4-b]pyridin-7-yl)acetamide.

In other embodiments, the compound has a structure represented by formula IIIb:

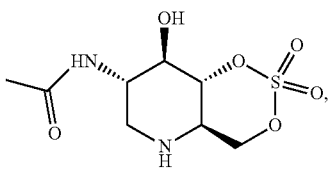
(IIIb)

or a pharmaceutically acceptable salt, solvate, or prodrug thereof.

A third aspect of the invention pertains to a compound have a structure represented by any of formulae (V)-(XI):

| Structure and Formula Number | Name |
|---|---|
| 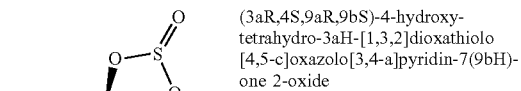<br>(V) | (3aR,4S,9aR,9bS)-4-hydroxy-tetrahydro-3aH-[1,3,2]dioxathiolo[4,5-c]oxazolo[3,4-a]pyridin-7(9bH)-one 2-oxide |
| 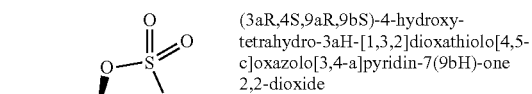<br>(VI) | (3aR,4S,9aR,9bS)-4-hydroxy-tetrahydro-3aH-[1,3,2]dioxathiolo[4,5-c]oxazolo[3,4-a]pyridin-7(9bH)-one 2,2-dioxide |
| 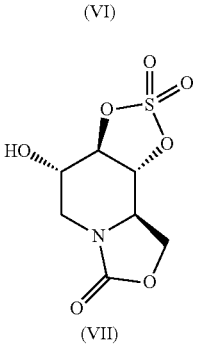<br>(VII) | (3aR,4S,9aR,9bR)-4-hydroxy-tetrahydro-3aH-[1,3,2]dioxathiolo[4,5-c]oxazolo[3,4-a]pyridin-7(9bH)-one 2,2-dioxide |

-continued

| Structure and Formula Number | Name |
|---|---|
| 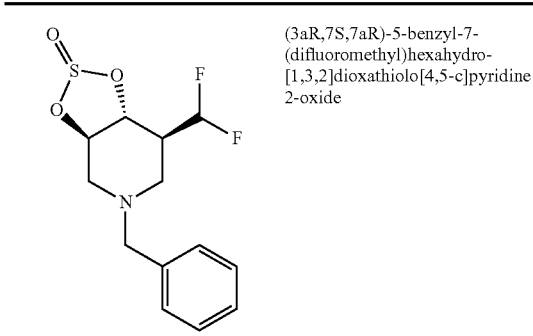<br>(VIII) | (3aR,7S,7aR)-5-benzyl-7-(difluoromethyl)hexahydro-[1,3,2]dioxathiolo[4,5-c]pyridine 2-oxide |
| 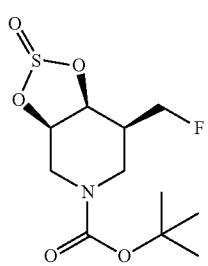<br>(IX) | (3aR,7S,7aR)-tert-butyl 7-(fluoromethyl)tetrahydro-[1,3,2]dioxathiolo[4,5-c]pyridine-5(6H)-carboxylate 2-oxide |
| 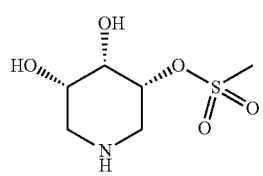<br>(X) | (3R,4S,5S)-4,5-dihydroxypiperidin-3-yl methanesulfonate |
| 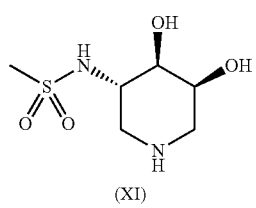<br>(XI) | N-((3S,4R,5S)-4,5-dihydroxypiperidin-3-yl)methanesulfonamide | or a pharmaceutically acceptable salt, solvate, or prodrug thereof.

Synthesis

Another aspect of the invention pertains to methods of producing the above compounds. For example, one method for producing the compound having formula IIIa comprises reacting N-benzyl(N-acetyl 1,2 dideoxynojiimycin) with SOCl$_2$ and pyridine. Compounds according to formula IIIa can be made according to the following synthesis Scheme 2:

Scheme 2:

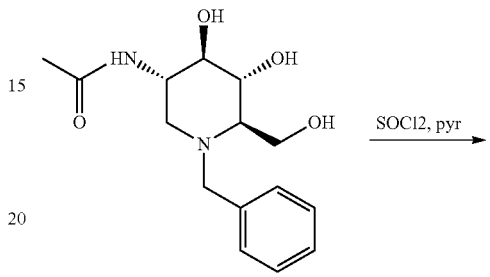

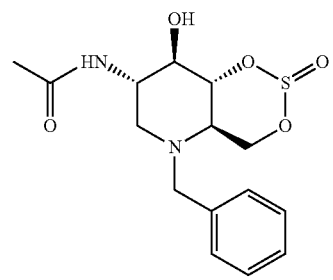

(IIIa)

Based on the above Scheme 2, one of ordinary skill in the art can produce the compounds according to formulae I-IV and IIIb by selecting different appropriate starting compounds. In particular, the sulfamates (where X=NR1R2) can be produced in a similar way) by using a sulfamoyl chloride.

Compounds according to formula V and VI may be produced by a method comprising reacting 1-deoxygalactonojirimycin with EtOCOCl to produce an intermediate, and reacting the intermediate with either SO$_2$Cl and pyridine or SO$_2$Cl$_2$ and pyridine. An exemplary process is shown in the following synthesis Scheme 3:

Scheme 3:

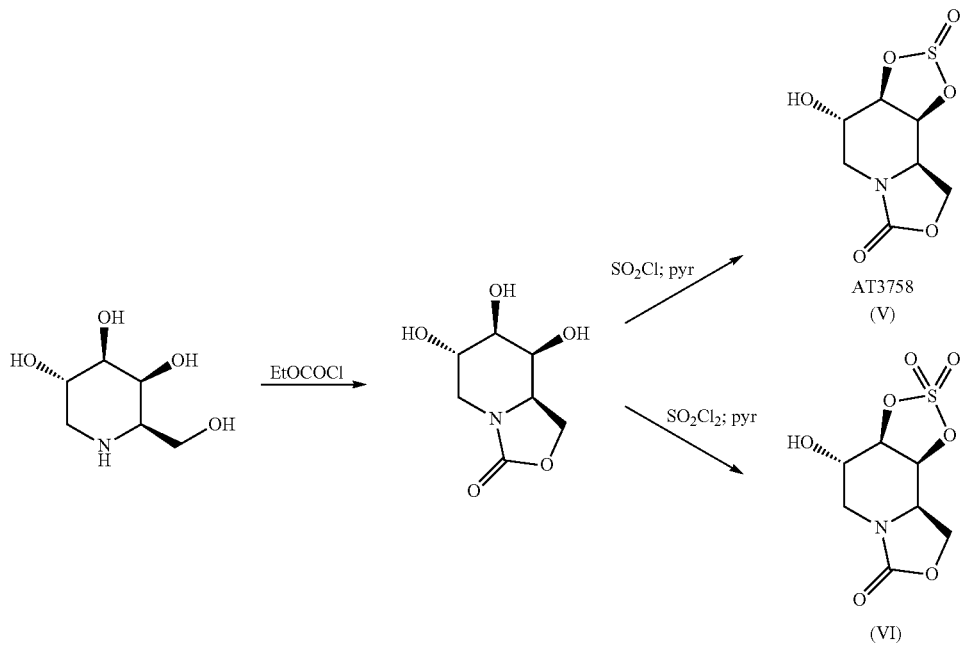

Compounds according to formula VIII can be made according to a method comprising reacting 1-deoxynojirimycin with EtOCOCl to produce an intermediate, and reacting the intermediate with SO$_2$Cl$_2$ and pyridine. An exemplary process is shown in the following synthesis Scheme 4:

Scheme 4:

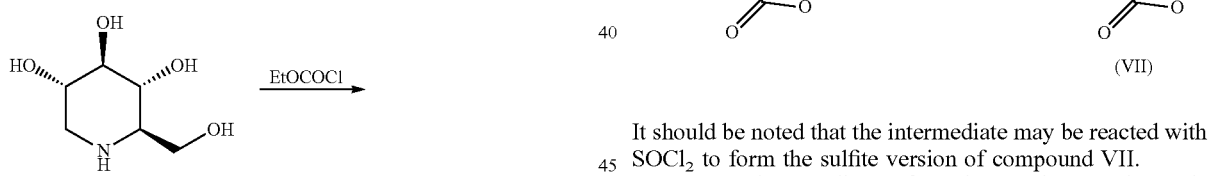

It should be noted that the intermediate may be reacted with SOCl$_2$ to form the sulfite version of compound VII.

Compounds according to formula X and XI can be made according to the following synthesis Scheme 5:

Scheme 5:

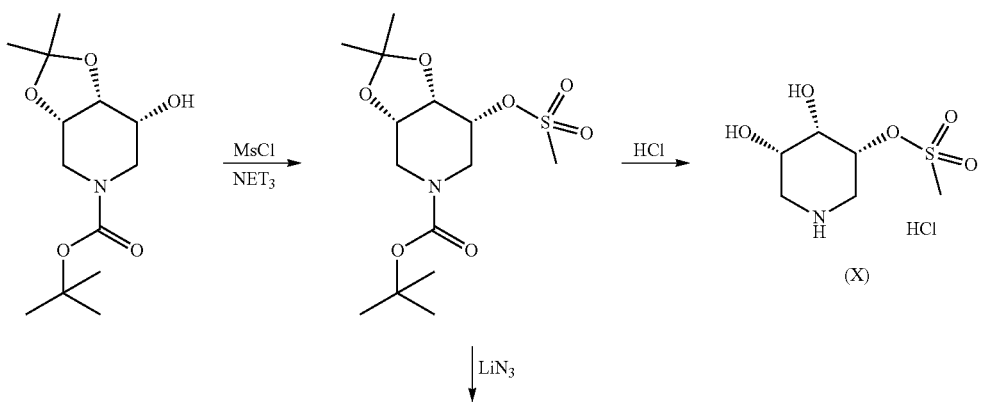

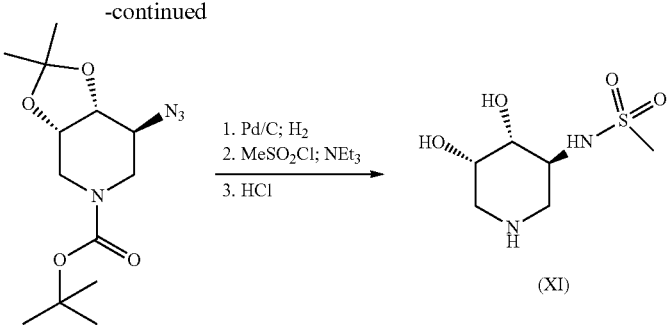

(XI)

Compounds according to formula IX can be made according to the following synthesis Scheme 6:

Scheme 6:

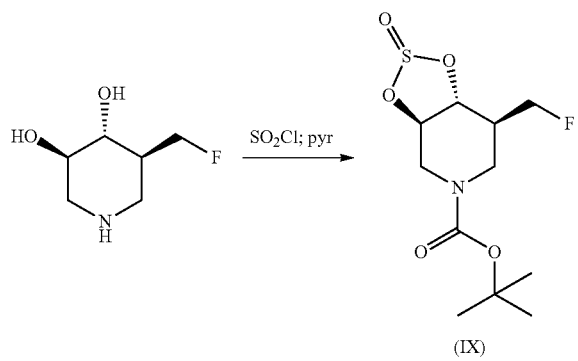

(IX)

Compounds according to formula VIII can be made according to the following synthesis Scheme 7:

Scheme 7:

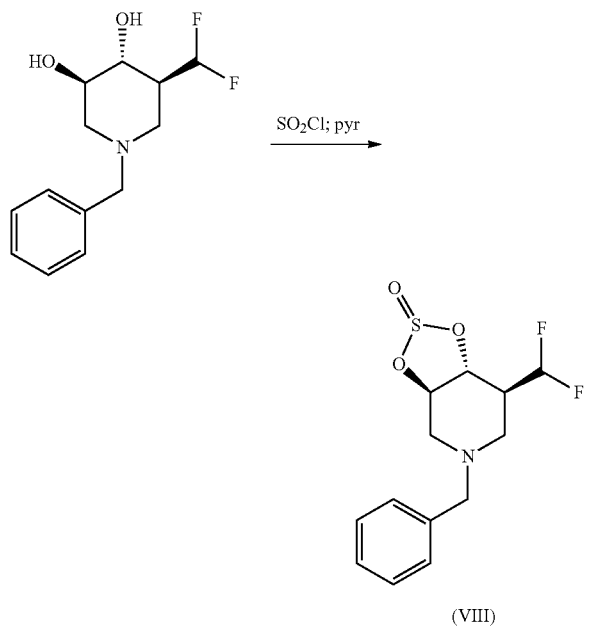

(VIII)

Compositions/Formulations

Other aspects of the invention pertain to compositions/formulations comprising any of the compounds described herein. Accordingly, one or more embodiments of the invention pertain to a pharmaceutical composition or formulation comprising: any of the compounds according to any of formulae (I)-(XI), or a pharmaceutically acceptable salt, solvate, or prodrug thereof; and at least one pharmaceutically acceptable carrier. The pharmaceutical composition may be prepared by adding a compound according to any of formulae (I)-(XI), or a pharmaceutically acceptable salt, solvate, or prodrug thereof to at least one pharmaceutically acceptable carrier.

Compounds of the present invention include pharmaceutically acceptable salts, solvates and pro-drugs of the compounds disclosed herein. Pharmaceutically acceptable salts include salts derived from inorganic bases such as Li, Na, K, Ca, Mg, Fe, Cu, Zn, Mn; salts of organic bases such as N,N'-diacetylethylenediamine, glucamine, triethylamine, choline, hydroxide, dicyclohexylamine, metformin, benzylamine, trialkylamine, thiamine; chiral bases like alkylphenylamine, glycinol, phenyl glycinol, salts of natural amino acids such as glycine, alanine, valine, leucine, isoleucine, norleucine, tyrosine, cystine, cysteine, methionine, proline, hydroxy proline, histidine, omithine, lysine, arginine, serine; non-natural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, hydrochlorides, sulphates, nitrates, phosphates, perchlorates, borates, hydrohalides, acetates, tartrates, maleates, citrates, succinates, palmoates, methanesulphonates, benzoates, salicylates, benzenesulfonates, ascorbates, glycerophosphates, ketoglutarates. In one embodiment, the pharmaceutically acceptable salt of the compounds disclosed herein is the hydrochloride salt.

"Solvate" denotes a physical association of a compound with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. "Hydrate" is a solvate wherein the solvent molecule is $H_2O$. Other non-limiting examples of suitable solvates include alcohols (e.g., ethanolates, methanolates, and the like).

Prodrugs are compounds which are converted in vivo to active forms (see, e.g., R. B. Silverman, 1992, "The Organic Chemistry of Drug Design and Drug Action", Academic Press, Chapter 8, incorporated herein by reference). Additionally, a discussion of prodrugs is provided in T. Higuchi and V. Stella, Pro-drugs as Novel Delivery Systems, Volume 14 of the A.C.S. Symposium Series, and in Bioreversible Carriers in Drug Design, Edward B. Roche, ed., American Pharmaceutical Association and Pergamon Press, 1987, both of which are incorporated herein by reference thereto. Prodrugs can be used to alter the biodistribution (e.g., to allow compounds which would not typically enter the reactive site of the protease) or the pharmacokinetics for a particular compound. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound with a suitable derivatizing agent. For example hydroxy groups can be converted into esters via treatment with a carboxilic acid in the presence of a catalyst. Examples of cleavable alcohol prodrug moieties include substituted and unsubstituted, branched or unbranched lower alkyl ester moieties, (e.g., ethyl esters), lower alkenyl esters, di-lower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

The compounds of the present invention can be formulated to be suitable for any route of administration, including e.g., orally in the form of tablets or capsules or liquid, or in sterile aqueous solution for injection. When the compound is formulated for oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); or preservatives (e.g., methyl or propyl-p-hydroxybenzoates or sorbic acid). The liquid preparations may also contain buffer salts, flavoring, coloring or sweetening agents as appropriate. Preparations for oral administration may be suitably formulated to give controlled or sustained release of the compound.

In some embodiments, the route of administration is subcutaneous. Other routes of administration may be oral or parenteral, including intravenous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation In one or more embodiments of the present invention, the compound is administered in a dosage form that permits systemic distribution or uptake, such that the compound may cross the blood-brain barrier so as to exert effects on neuronal cells. Such dosage forms that permit systemic distribution or uptake may be oral or parenteral. In some embodiments, the compound may be distributed systemically, including crossing the blood-brain barrier.

For example, pharmaceutical formulations of the compound suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, polyethylene glycol, and the like), suitable mixtures thereof, or vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate or gelatin.

Sterile injectable solutions are prepared by incorporating the compound in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a commonly used excipient.

The formulation can also contain a non-ionic detergent. Examples of non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

Kits & Methods of Treatment

Another aspect of the invention pertains to a kit comprising: a container having an effective amount of any of the compounds according to any of formulae (I)-(IV), or a pharmaceutically acceptable salt, solvate, or prodrug thereof, or any combination of two or more thereof; and instructions for using the same to prevent and/or treat MPS IIIC. In one or more embodiments, the kit further comprises an effective amount of a second therapeutic agent, such as a recombinant MPS IIIC enzyme.

Accordingly, yet another aspect of the invention pertains to a method of preventing and/or treating MPS IIIC, the method comprising administering to a patient in need thereof a therapeutically effective amount of any of the compounds discussed above. In particular, the compounds used to treat MPS IIIC may be any of the compounds according to any of formulae (I)-(IV), or a pharmaceutically acceptable salt, solvate, or prodrug thereof, or any combination of two or more thereof. In one or more embodiments, the method further comprises administering an effective amount of a second therapeutic agent. For example, the second therapeutic agent may comprise a recombinant MPS IIIC enzyme. The recombinant MPS IIIC may be administered via enzyme replacement therapy (ERT).

The therapeutic agent(s) may be administered orally or parenterally, including intravenously, subcutaneously, intraarterially, intraperitoneally, ophthalmically, intramuscularly, buccally, rectally, vaginally, intraorbitally, intracerebrally, intradermally, intracranially, intraspinally, intraventricularly, intrathecally, intracisternally, intracapsularly, intrapulmonarily, intranasally, transmucosally, transdermally, or via inhalation. In one preferred embodiment, the therapeutic agent(s) is administered orally.

Administration of therapeutic agent(s) may be by periodic injections of a bolus of the formulation, or may be administered by intravenous or intraperitoneal administration from a reservoir which is external (e.g., an i.v. bag) or internal (e.g., a bioerodable implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780, 014, and 5,814,607, each incorporated herein by reference. Other useful parenteral delivery systems include ethylenevinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Subcutaneous injections have the advantages allowing self-administration, while also resulting in a prolonged plasma half-life as compared to intravenous administration. Furthermore, a variety of devices designed for patient convenience, such as refillable injection pens and needle-less injection devices, may be used with the formulations of the present invention as discussed herein.

A suitable pharmaceutical preparation is in a unit dosage form. In such form, the preparation is subdivided into suitably sized unit doses containing appropriate quantities of the active component, e.g., an effective amount to achieve the desired purpose such as maximizing substrate clearance.

The amount of effective therapeutic agent(s) for preventing or treating the referenced disorder can be determined on a case-by-case basis by those skilled in the art, guided by the present specification and the examples herein. The amount and frequency of administration of the therapeutic agent(s) will be regulated according to the judgment of the attending clinician (physician) considering such factors as age, condition and size of the patient as well as risk for developing disorder or severity of the symptoms of the referenced disorder being treated.

The therapeutic agent(s) of the present invention can be administered in combination with at least one other therapeutic agent. Administration of the therapeutic agent(s) of the present invention with at least one other therapeutic agent is understood to encompass administration that is sequential or concurrent. In one embodiment, the therapeutic agents are administered in separate dosage forms. In another embodiment, two or more therapeutic agents are administered concurrently in the same dosage form.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A compound having a structure represented by formula III:

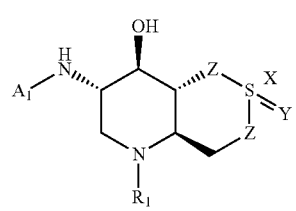

wherein: $A_1$ is acetyl;
$R_1$ is H, arylalkyl, aryl, or $C_{1-4}$ alkyl;
X and Y are each independently O or a lone pair of electrons; and each Z is O; or
a pharmaceutically acceptable salt, or solvate thereof.

2. The compound of claim 1, wherein the compound has a structure represented by formula IIIa:

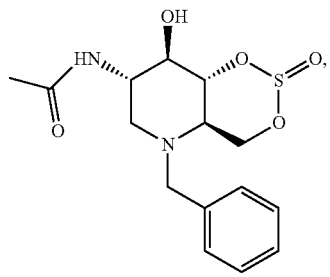
(IIIa)

or or a pharmaceutically acceptable salt, or solvate thereof.

3. The compound of claim 1, wherein the compound has a structure represented by formula IIIb:

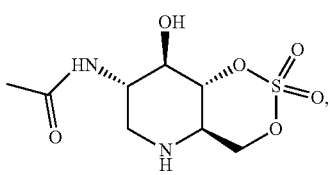
(IIIb)

or or a pharmaceutically acceptable salt, or solvate thereof.

4. A compound have a structure represented by any of formulae (V)-(XI):

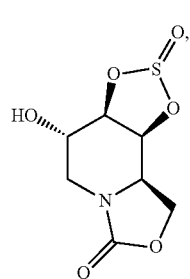
(V)

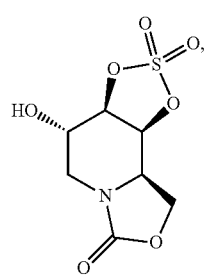
(VI)

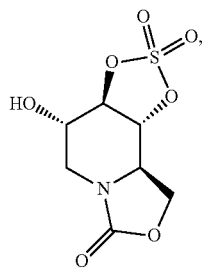
(VII)

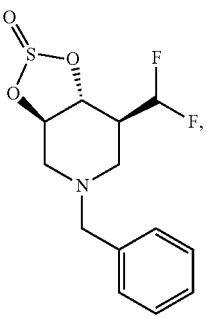
(VIII)

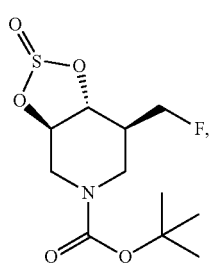
(IX)

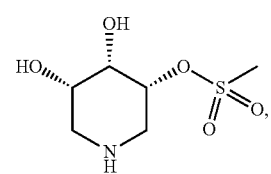
(X)

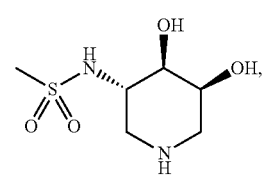
(XI)

or or a pharmaceutically acceptable salt, or solvate thereof.

* * * * *